United States Patent [19]
Mittermeier

[11] Patent Number: 6,050,954
[45] Date of Patent: Apr. 18, 2000

[54] BIOPSY NEEDLE ORIENTATION FIXTURE

[75] Inventor: Manfred Mittermeier, Northfield, Ill.

[73] Assignee: Manan Medical Products, Inc., Northbrook, Ill.

[21] Appl. No.: 09/138,245

[22] Filed: Aug. 21, 1998

[51] Int. Cl.[7] .................................................. A61B 10/00
[52] U.S. Cl. ......................................... 600/562; 606/130
[58] Field of Search .................................... 600/461, 464, 600/562, 564–567; 606/130

[56] References Cited

U.S. PATENT DOCUMENTS

| | | | |
|---|---|---|---|
| 2,697,433 | 12/1954 | Zehnder | 128/83 |
| 3,262,452 | 7/1966 | Hardy et al. | 128/303 |
| 4,230,117 | 10/1980 | Anichkov | 128/303 |
| 4,350,159 | 9/1982 | Gouda | 128/303 |
| 4,463,758 | 8/1984 | Patil et al. | 128/303 B |
| 4,727,565 | 2/1988 | Ericson | 378/205 |
| 4,838,506 | 6/1989 | Cooper | 248/200 |
| 5,052,396 | 10/1991 | Wedel et al. | 128/662.05 |
| 5,056,523 | 10/1991 | Hotchkiss et al. | 606/130 |
| 5,078,142 | 1/1992 | Siczek et al. | 128/653.1 |
| 5,280,427 | 1/1994 | Magnusson et al. | 600/567 |
| 5,426,685 | 6/1995 | Pellegrino et al. | 378/87 |
| 5,623,931 | 4/1997 | Wung et al. | 128/662.05 |

OTHER PUBLICATIONS

*Horizontal Sterotactic Needle Guide* Product Brochure by BIP USA Inc. Rev. Jun. 8, 1993.
*Cytoguide/mammo Diagnost 3000* Operator's Manual by Phillips Medical Systems.
*The MF–150 Mammography System* Product Brochure by Bennett X–Ray Corp.
*HF–X* Product Brochure by Fischer Imaging.
*Alpha III* Product by Instrumentarium Imaging.

*Primary Examiner*—Max Hindenburg
*Attorney, Agent, or Firm*—Dick and Harris

[57] ABSTRACT

The present invention is directed to a biopsy needle orientation fixture for use in association with diagnostic mammography equipment, and in particular, a horizontal stereotactic mammography x-ray machine having a radiation source. The biopsy needle orientation fixture comprises a substantially L-shaped frame having both horizontal and vertical members. The horizontal and vertical members are joined at one end, while the second end of the horizontal member houses a vertical needle guide, and the second end of the vertical member houses a horizontal needle guide. The horizontal and vertical needle guides allow a biopsy procedure to be performed accurately along both vertical and horizontal needle pathways. The fixture further comprises a means for mounting the substantially L-shaped frame to the stereotactic mammography x-ray machine, and a displacement from alignment with the horizontal needle path in the horizontal member. This displacement from alignment allows radiation to image and identify the horizontal needle position both before and after a breast lesion is biopsied.

11 Claims, 1 Drawing Sheet

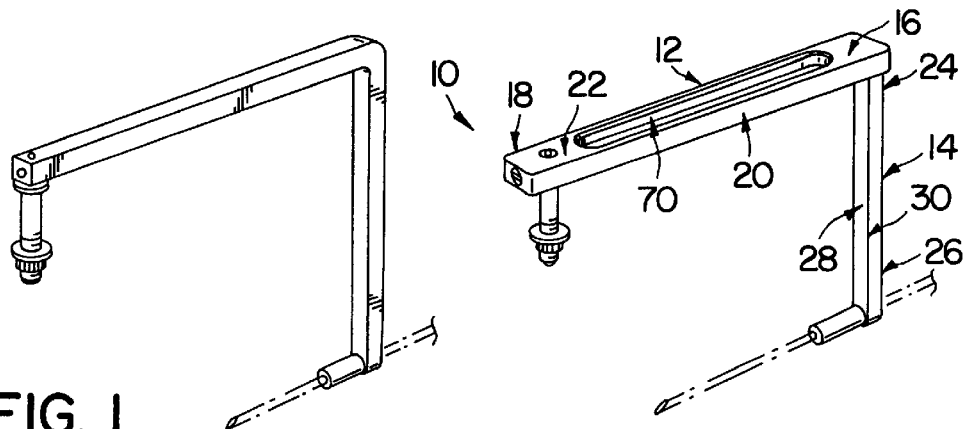
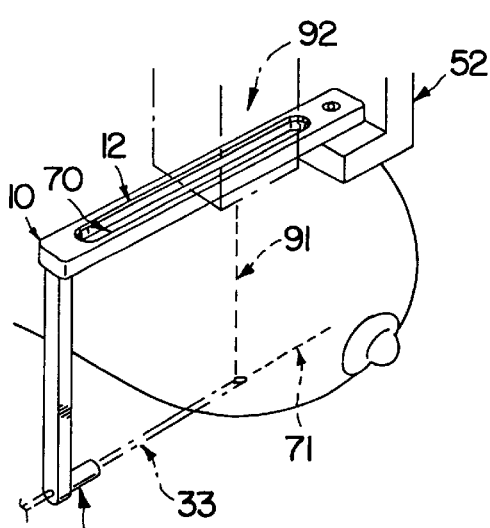
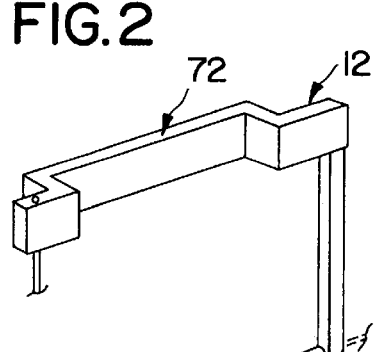
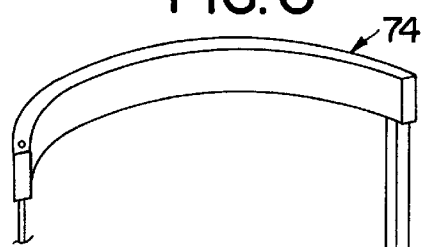
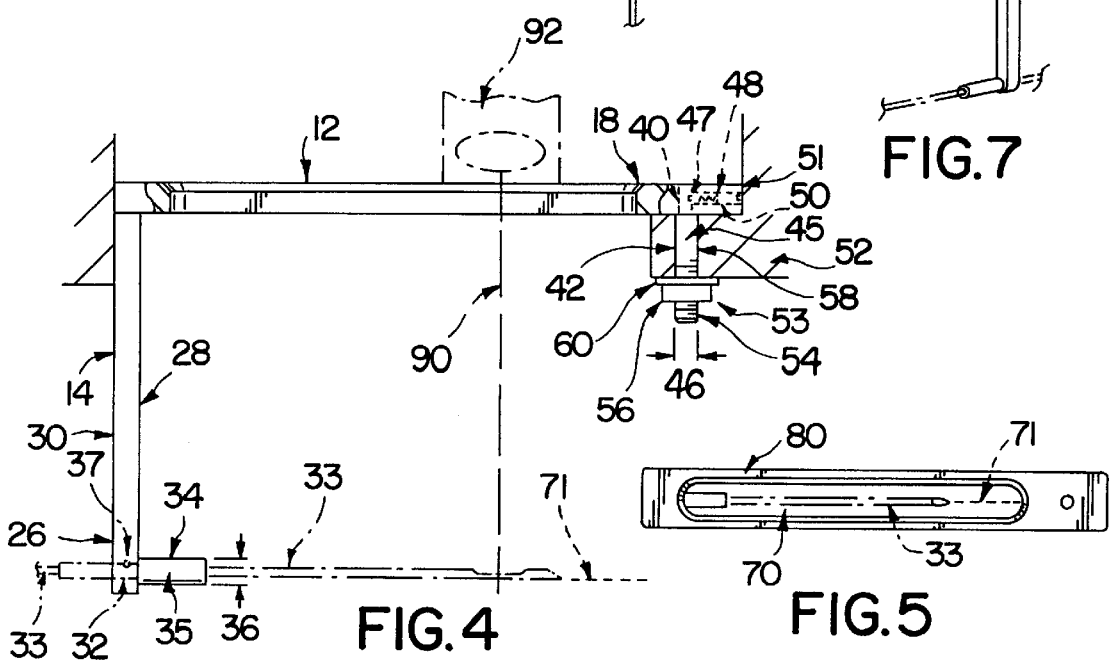

BIOPSY NEEDLE ORIENTATION FIXTURE

BACKGROUND OF THE INVENTION

1. Field of the Invention

The present invention relates in general to medical devices, and, more particularly, to a biopsy needle orientation fixture for use in association with a biopsy needle and diagnostic mammography equipment having a radiation source.

2. Background of the Invention

Biopsy needles have been used in association with mammography x-ray machines for several years. In particular, many of these mammography machines have some form of a vertical biopsy needle guide, to facilitate biopsy procedures. This vertical guide allows a biopsy needle to be positioned over a lesion or other pre-determined region in a breast, and to enter the breast along a vertical pathway leading to the lesion or pre-determined region. Because it defines a biopsy needle path, this type of device allows for consistency in breast biopsy procedures.

While these vertical mammography machines have enjoyed considerable success, many physicians have desired not only vertical biopsy capabilities, but also horizontal biopsy capabilities. Although vertical needle entry allows biopsy procedures to be performed on most lesions in a breast, vertical entry is not well-suited for lesions near the surface, but lower in the breast. Specifically, in such surficial-type lower breast lesions, vertical entry forces the biopsy needle to pass through a large portion of the breast. In contrast, horizontal entry to such lesions requires a much shorter puncture track into the breast. Moreover, horizontal entry capabilities also allow a wider variety of breast entry sites. This variety is especially useful for lesions near the chest wall, which may be biopsied via a horizontal entry site at least partially perpendicular to the chest wall.

Accordingly, devices have been created for use with stereotactic mammograph x-ray machines, to facilitate vertical and horizontal biopsy procedures. One such prior art device, shown in FIG. 1, is an L-shaped fixture with horizontal and vetical legs, and both vertical and horizontal needle guides. Such a device is attached to a stereotactic mammography x-ray machine so that the horizontal needle guide swings in a precise arc about a vertical axis defined by the vertical needle guide. Accordingly, the fixture may be oriented for an unlimited number of horizontal breast entry sites, all of which intersect the vertical entry path defined by the vertical needle guide.

However, although such a prior art device provides both horizontal and vertical needle entry capabilities, it was not well-suited for use in association with a mammography unit having a radiation source mounted above the L-shaped fixture. In particular, because of the beneficial L-shaped structure of the prior art fixture, the horizontal leg is aligned with the horizontal needle pathway. Consequently, the horizontal leg blocks radiation emitted from a radiation source positioned above the fixture, and prevents x-ray imaging of the needle position relative to a breast lesion.

Accordingly, it is a goal in the art to provide a biopsy needle fixture, having both horizontal and vertical biopsy capabilities, for use with diagnostic mammography x-ray equipment, while also providing a device that allows a radiation source to locate and identify horizontal biopsy needle positions within the target area of a breast. These and other objectives for the invention are described herein.

SUMMARY OF THE INVENTION

The present invention is directed to a biopsy needle orientation fixture for use in association with mammography diagnostic equipment and, more particularly, a horizontal stereotactic mammography x-ray machine having a radiation source. The biopsy needle orientation fixture comprises a substantially L-shaped frame having both a horizontal and a vertical member.

The horizontal and vertical members are joined at one end, while the horizontal member has a vertical aperture formed proximate its second end, and the vertical member has a horizontal aperture formed proximate its second end. A horizontal needle guide is positioned in the horizontal aperture in the vertical member. Likewise, a vertical needle guide is positioned in the vertical aperture in the horizontal member. Moreover, while the vertical needle guide defines a vertical needle path, the horizontal needle guide defines a horizontal needle path.

The inside diameter of the horizontal and vertical needle guides is slightly larger than the outer diameter of an associated biopsy needle. This relationship allows the biopsy needle to slide freely through the needle guides, yet preferably remain in some degree of frictional contact therewith for optimal needle control. In a preferred embodiment, the horizontal and vertical needle guides are removable and replaceable to allow for use of the biopsy needle orientation fixture with biopsy needles of varying diameters.

In another preferred embodiment, the horizontal needle guide extends beyond the outer face of the vertical member, so as to allow for more control and stability of the biopsy needle when performing a biopsy along the horizontal needle path.

The biopsy needle orientation fixture includes at least a portion of the horizontal member being displaced from alignment with the horizontal needle path such that the biopsy needle can be visualized by the radiation source positioned above the fixture. In a preferred embodiment, the displacement of the horizontal member from alignment with the horizontal needle path comprises a horizontal slot formed through the horizontal member between its first end and the vertical aperture. The horizontal slot is in substantial registration with the horizontal needle path, thus allowing radiation emitted from a source above the fixture to pass through the slot and image the horizontal biopsy needle position inside a breast.

In another preferred embodiment, the displacement of the horizontal member from alignment with the horizontal needle pathway comprises an offset within the horizontal member. Like the horizontal slot, the offset permits radiation to image a biopsy needle extending along the horizontal needle path.

In yet another preferred embodiment, the displacement of the horizontal member from alignment with the horizontal needle path comprises at least a portion of the horizontal member having an arcuate shape. This shape functions much like the offset in facilitating a direct radiation pathway to the horizontal needle path.

Inasmuch as x-rays of the biopsy needle position are preferably taken both before and after the actual sampling of the lesion—to ensure that the biopsy sample is taken from the proper region of the breast—the displacement of the horizontal member from alignment with the horizontal needle pathway allows x-ray images to be taken from an x-ray source positioned above the breast. This convenient and conventional x-ray imaging position, in turn, eliminates the need for a physician or technician to re-orient the mammography machine for x-ray purposes while the biopsy needle is in the breast of a patient, thus making the biopsy procedure more patient-friendly.

Finally, the biopsy needle orientation fixture consists of a means for mounting the substantially L-shaped frame to the stereotactic horizontal mammography x-ray machine. The mounting means preferably consists of at least a portion of the exterior surface of the vertical needle guide having threads to accept a fastening member such as a screw or nut. Such a means facilitates rotation of the vertical member and horizontal needle guide about the vertical axis running through the vertical needle guide and along a continuous arc—thus allowing horizontal needle entry at an unlimited number of sites on a breast. However, any conventional mounting means allowing similar arcuate movement of the horizontal needle guide is likewise contemplated.

BRIEF DESCRIPTION OF THE DRAWINGS

FIG. 1 is a perspective view of a prior art biopsy needle orientation fixture;

FIG. 2 is a perspective view of the biopsy needle orientation fixture according to one embodiment of the present invention;

FIG. 3 is a perspective view of the biopsy needle orientation fixture affixed to a portion of a stereotactic mammography x-ray machine and positioned to perform a horizontal biopsy on a breast according to the present invention;

FIG. 4 is a side elevational view of the biopsy needle orientation fixture according to the present invention;

FIG. 5 is a top plan view of the biopsy needle orientation fixture of FIG. 4, with a biopsy needle extending through the horizontal needle guide according to the present invention;

FIG. 6 is a perspective view of the biopsy needle orientation fixture according to another embodiment of the present invention; and FIG. 7 is a perspective view of the biopsy needle orientation fixture according to yet another embodiment of the present invention.

DETAILED DESCRIPTION OF THE DRAWINGS

While the present invention is susceptible of embodiment in many different forms, there is shown in the drawings and will be herein described in detail several specific embodiments with the understanding that the present disclosure is to be considered as an exemplification of the principles of the invention and is not intended to limit the invention to the embodiments illustrated.

Biopsy needle orientation fixture 10 for use in association with diagnostic mammography equipment having a radiation source is shown in FIG. 2. Biopsy needle orientation fixture 10 comprises a substantially L-shaped frame consisting of horizontal member 12 and vertical member 14. Although it is contemplated that biopsy needle orientation fixture 10 may be used in association with any number of types of diagnostic mammography equipment, the present invention will be described specifically in relation to a horizontal stereotactic mammography x-ray machine.

Horizontal member 12 comprises first end 16, second end 18, inner face 20, and outer face 22. Likewise, vertical member 14 also comprises first end 24, second end 26, inner face 28, and outer face 30. Although the horizontal and vertical members are pictured as taking the form of substantially solid rectangular bars, it is also contemplated they may take any desired shape, such as substantially cylindrical bars.

First end 16 of horizontal member 12 is affixed to first end 20 of vertical member 14. Preferably, inasmuch as horizontal member 12 is generally wider than vertical member 14, first end 24 of the vertical member is joined to inner face 22 of first end 16 of the horizontal member. However, a reverse attachment, with first end 16 of the horizontal member joined to inner face 28 of vertical member 14, is likewise contemplated. In either case, vertical member 14 is in a substantially perpendicular relationship to horizontal member 12.

As can best be seen in FIG. 4, second end 26 of vertical member 14 further consists of horizontal aperture 32, which is of an appropriate diameter to accept horizontal needle guide 34. Horizontal needle guide 34 comprises an outer cylindrical tube 35 defining an inner diameter. Although the inner diameter remains substantially consistent throughout the length of horizontal needle guide 34, it is preferred that at least a portion of the horizontal needle guide has an outer diameter 36 that is larger than the interior diameter of horizontal aperture 32. This difference in horizontal needle guide outer diameters forms a ridge which, in turn, acts as a stop when inserting the horizontal needle guide into the horizontal aperture. Moreover, while horizontal needle guide 34 is at least partially secured in horizontal aperture 32 by an interference fit, outer tube 35 further consists of a small hole capable of cooperating with a spring loaded detent 37 positioned on the inner surface of horizontal aperture 32. Such a securing mechanism allows the horizontal needle guide to be removed and replaced to accommodate biopsy needles of varying diameters.

Moreover, outer tube 35 of horizontal needle guide 34 may also consist of another hole opposite the first hole. This second hole, in cooperation with a bore hole in the bottom of second end 26 of vertical member 14, allows direct depression of the spring loaded detent for easier removal and replacement of the horizontal needle guide.

Furthermore, while FIG. 2 shows horizontal needle guide 34 flush with outer face 30 of vertical member 14, it is likewise contemplated and shown in FIG. 4 that the horizontal needle guide may extend through horizontal aperture 32 and past outer face 30 of vertical member 14. Such an embodiment extends the length of the horizontal needle guide, thus allowing a greater portion of the biopsy needle to be encased in the horizontal needle guide. This increased encasement, in turn, provides increased stabilization for biopsy needle 33. Indeed, the biopsy needle is not only required to be inserted into and retracted from a patient's breast along a specific path, but the needle also remains at the same position inside the breast during x-ray imaging of needle location before biopsy sampling, during the biopsy procedure, and during x-ray imaging of needle location after biopsy sampling. Notably, the horizontal needle guide is lengthened without extending the guide any further toward an intended target such as a breast, which would reduce the arcuate range of the horizontal needle guide.

Referring still to FIG. 4, second end 18 of horizontal member 12 consists of vertical aperture 40, which is of an appropriate diameter to accept vertical needle guide 42. Like the horizontal needle guide, vertical needle guide 42 comprises an outer cylindrical tube 45 defining an inner diameter. Although the inner diameter remains constant through the length of vertical needle guide 42, it is preferred that at least a portion of the vertical needle guide has an outside diameter 46 that is larger than the interior diameter of the vertical aperture 40. Moreover, also like the horizontal needle guide, this difference in vertical needle guide outer tube diameters forms a ridge which, in turn, acts as a stop when inserting the vertical needle guide into the vertical aperture.

While vertical needle guide 42 is at least partially secured in vertical aperture 40 by an interference fit, outer tube 45 further consists of a small hole capable of cooperating with a spring loaded detent 47 positioned on the inner surface of vertical aperture 40. The spring loaded detent is preferably integrated into a set screw 48, which enters the horizontal member 12 through a threaded bore hole 50 extending from the outer edge 51 of second end 18 of the horizontal member to vertical aperture 40. Similar to detent 37, such a securing mechanism allows the horizontal needle guide to be removed and replaced to accommodate biopsy needles of varying diameters.

Of course, selection of horizontal and vertical needle guides depends on the outer diameter of the biopsy needle. The outer diameter of biopsy needle should be slightly smaller than the inner diameter of the horizontal and vertical needle guides, so as to allow the biopsy needle to slide freely through the needle guides along vertical and horizontal paths, respectively.

As is shown in FIGS. 3 and 4, vertical needle guide 42 further consists of a means 53 for mounting biopsy needle orientation fixture 10 to horizontal stereotactic x-ray machine 52. Mounting means 53 preferably consists of at least a portion of the exterior surface of the vertical needle guide having threads 54 on at least a portion of its exterior surface. Threads 54 allow a fastening member 56, such as a nut or a screw, to securely clamp fixture 10 to horizontal stereotactic x-ray machine 52 after vertical needle guide 42 is inserted through a corresponding hole 58 in the machine. Additionally, washer 60, or other similar bracing member, may be used in combination with fastening member 56 for improved stabilization or fit. Of course, the size of vertical needle guide 52, the size of threaded portion 54, and fastening member 56 may be adjusted to accommodate mammography machines of differing dimensions.

Such a mounting means facilitates rotation of vertical member 14 and horizontal needle guide 34 about the vertical axis running through vertical needle guide 42 and along a continuous arc—thus allowing horizontal needle entry into a breast at an unlimited number of sites. To this end, any conventional mounting means allowing similar arcuate movement of the horizontal needle guide is likewise contemplated.

Horizontal member 12 further consists of a portion of the horizontal member being displaced from alignment with horizontal needle path 71 such that biopsy needle 33 can be visualized by a radiation source positioned above biopsy orientation fixture 10. In one embodiment, shown in FIG. 2, the displacement from alignment with the horizontal needle path comprises an elongated horizontal slot 70 spanning a majority of horizontal member 12. As is shown in FIG. 5, horizontal slot 70 extends through the thickness of the horizontal member, and allows radiation to pass through the horizontal member to image horizontal needle path 71.

In another embodiment, shown in FIG. 6, the displacement from alignment with the horizontal needle path comprises offset 72 spanning a majority of horizontal member 12. Although shown extending to the right of the horizontal needle path, offset 72 may extend to either side thereof. Likewise, while offset 72 is pictured as taking a substantially rectangular form, it is likewise contemplated that offset 72 may be substantially arcuate, triangular, or other shape allowing access to the horizontal needle path.

In yet another embodiment, illustrated in FIG. 7, the displacement from alignment with the horizontal needle path comprises arcuate horizontal member 74. Like horizontal slot 70 of FIG. 2 and offset 72 of FIG. 6, arcuate horizontal member 74 allows radiation access to the horizontal needle pathway.

Moreover, it is also contemplated that horizontal 12 member may further consist of markings 80 on its outer face 20 (see FIG. 5). Markings 80, such as a scale or ruler, may facilitate location of biopsy needle 33 relative to a set point, such as a lesion, in a patient's breast.

In operation, and referring to FIG. 3, biopsy needle orientation fixture 10 is affixed to stereotactic mammography x-ray machine 52. Upon proper identification of a breast lesion, the fixture is adjusted so that the horizontal and vertical needle guides are centered on the lesion. Assuming a horizontal biopsy procedure, biopsy needle 33 is inserted through horizontal needle guide 34. Inasmuch as insertion of biopsy needle 33 through horizontal needle guide 34 directs the needle along a horizontal path directly below and in alignment with the center of horizontal member 12, displacement from alignment with the horizontal needle path, for example horizontal slot 70, allows radiation 90 to image the breast along the horizontal needle path. As a result, and unlike prior art biopsy needle orientation devices, the biopsy needle may be imaged in its horizontal position by radiation source 92 positioned directly above the biopsy orientation fixture.

This ability to photograph the needle position from directly above the biopsy needle orientation fixture is particularly advantageous given that the radiation source in most horizontal stereotactic x-ray machines is directly above the orientation fixture. Inasmuch as it is preferable to take x-rays of the needle in the breast before the actual tissue sample is taken—to ensure proper location of the needle relative to the lesion—and after the tissue sample is taken—to ensure that a patient's movements do not affect sampling of the specific target tissue area—the needle is required to remain in the patient for an extended period of time. Accordingly, the ability of a mammography x-ray machine operator to have quick, easy access to an x-ray unit positioned directly over the reorientation fixture, and the elimination of any need to take x-rays from different angles because the reorientation fixture blocks direct needle exposure, are benefits realized by both patients and mammography machine operators. Indeed, patient discomfort is minimized by reducing the number of x-rays taken and, in turn, the time it takes to take those x-rays.

Finally, inasmuch as the present invention is designed to facilitate precision in biopsy procedures, the biopsy needle orientation fixture is preferably constructed from a rigid, durable material, such as steel, steel alloys, or other metal alloys. This strength and rigidity ensure biopsy procedures that are consistent, accurate, and reliable.

The foregoing description and drawings merely explain and illustrate the invention and the invention is not limited thereto except insofar as the appended claims are so limited, as those skilled in the art who have the disclosure before them will be able to make modifications and variations therein without departing for the scope of the invention.

What is claimed is:

1. A biopsy needle orientation fixture for use in association with a biopsy needle and diagnostic mammography equipment, said diagnostic mammography equipment including a radiation source, said biopsy needle having an outer diameter, said biopsy needle orientation fixture comprising:

a substantially L-shaped frame, said substantially L-shaped frame having vertical and horizontal members, each of said vertical and horizontal members having a first end and a second end opposite said first end, an inner face and an outer face opposite said inner face, said vertical and horizontal members being joined at said first end thereof;

a substantially vertical aperture formed proximate said second end of said horizontal member for insertion of a vertical needle guide, said vertical needle guide disposed on and perpendicular to said inner face of said horizontal member in registration with said substantially vertical aperture, said substantially vertical aperture and vertical needle guide having an inner diameter at least slightly larger than said outer diameter of said biopsy needle such that said biopsy needle is operably slidable through said substantially vertical aperture and vertical needle guide along a vertical path intersecting a lesion within a compressed breast;

a substantially horizontal aperture formed proximate said second end of said vertical member for insertion of a horizontal needle guide, said horizontal needle guide being disposed on and perpendicular to said inner face of said vertical member in registration with said horizontal aperture, said horizontal aperture and horizontal needle guide having an inner diameter at least slightly larger than said outer diameter of said biopsy needle such that said biopsy needle is operably slidable through said substantially horizontal aperture and horizontal needle guide along a horizontal path intersecting said lesion within said compressed breast, at least a portion of said horizontal member being displaced from alignment with said horizontal path such that said biopsy needle can be visualized by said diagnostic mammography equipment from directly above said biopsy needle orientation fixture; and means for mounting said substantially L-shaped frame to said diagnostic mammography equipment in operable association with said radiation source.

2. The invention according to claim 1 wherein said displacement of said horizontal member from alignment with said horizontal path comprises a substantially elongated horizontal slot formed through said horizontal member from its outer face to its inner face between said first end and said vertical aperture, said slot being in substantial registration with said horizontal path.

3. The invention according to claim 2 wherein said horizontal slot longitudinally spans a majority of said horizontal member.

4. The invention according to claim 1 wherein said displacement of said horizontal member from alignment with said horizontal path comprises an offset within said horizontal member of said substantially L-shaped frame.

5. The invention according to claim 4 wherein said offset encompasses a majority of said horizontal member.

6. The invention according to claim 1 wherein said displacement of said horizontal member from alignment with said horizontal path comprises at least a portion of said horizontal member of said substantially L-shaped frame having an arcuate shape.

7. The invention according to claim 1 wherein said horizontal needle guide is configured so as to be capable of being removed from said horizontal member and replaced to allow cooperation with biopsy needles having different outer diameters.

8. The invention according to claim 1 wherein said vertical needle guide is configured so as to be capable of being removed from said horizontal member and replaced to, in turn, allow cooperation with biopsy needles having different outer diameters.

9. The invention according to claim 1 wherein said horizontal member includes markings on its outer face to facilitate location of a biopsy needle, operably positioned in said horizontal needle guide, relative to a set point in said breast.

10. The invention according to claim 1 wherein said means for mounting said substantially L-shaped frame to said diagnostic mammography equipment comprises said vertical needle guide, having an exposed exterior surface, having threads on at least a portion of its exposed exterior surface;

a fastening member operably adjustable on said vertical needle guide threaded exposed exterior surface for clamping a portion of said diagnostic mammography equipment.

11. The invention according to claim 1 wherein said horizontal needle guide extends through said horizontal aperture in said vertical member and beyond the outer face of said vertical member.

* * * * *